(12) United States Patent
Ito et al.

(10) Patent No.: US 6,699,487 B2
(45) Date of Patent: Mar. 2, 2004

(54) COSMETICS

(75) Inventors: Eizo Ito, Tokyo (JP); Naoki Ito, Tokyo (JP)

(73) Assignee: Shinei Fermentec Corporation, Tokyo (JP)

( * ) Notice: Subject to any disclaimer, the term of this patent is extended or adjusted under 35 U.S.C. 154(b) by 0 days.

(21) Appl. No.: 09/929,064

(22) Filed: Aug. 15, 2001

(65) Prior Publication Data

US 2003/0035817 A1 Feb. 20, 2003

(51) Int. Cl.[7] ............... A61K 7/00; A61K 35/70; A61K 7/06; A61K 7/42
(52) U.S. Cl. ............... 424/401; 424/195.16; 424/74; 424/59
(58) Field of Search ............... 424/401, 74, 59, 424/195.16

(56) References Cited

U.S. PATENT DOCUMENTS

| 3,998,761 A | * | 12/1976 | Gary et al. | 424/70.13 |
|---|---|---|---|---|
| 4,194,018 A | | 3/1980 | Hodel et al. | |
| 4,232,122 A | * | 11/1980 | Zilliken | 252/407 |
| 5,006,337 A | * | 4/1991 | Motitschke et al. | 424/74 |
| 5,753,640 A | * | 5/1998 | Araneo et al. | 514/178 |
| 5,824,702 A | * | 10/1998 | Wei | 424/59 |
| 6,020,367 A | * | 2/2000 | Duffy et al. | 424/401 |

FOREIGN PATENT DOCUMENTS

| CN | 1123833 | 6/1996 |
|---|---|---|
| JP | 81009902 B | 3/1981 |
| JP | 57-125669 | 8/1982 |
| JP | 59-6856 | 1/1984 |
| JP | 1-231865 | 9/1989 |

* cited by examiner

Primary Examiner—Shengjun Wang
(74) Attorney, Agent, or Firm—Sughrue Mion, PLLC

(57) ABSTRACT

The present invention provides a cosmetic comprising a superoxide scavenger containing a desirable material which is different from any conventional unstable superoxide dismutase and is available at a low cost. The cosmetic of the present invention comprises a superoxide scavenger including a composition extracted from a specific liquid. This specific liquid is prepared by: boiling a grain with a liquid to obtain a grain liquor; cooling the obtained grain liquor; adding a yeast into the cooled grain liquor; leaving the grain liquor with the yeast while supplying oxygen thereto; and sterilizing the resulting liquid by heating to obtain the specific liquid.

10 Claims, No Drawings

COSMETICS

FIELD OF THE INVENTION

The present invention relates to a cosmetic, and more particularly to a cosmetic containing a superoxide scavenger.

BACKGROUND OF THE INVENTION

It is known that superoxide, or free radical $O_2^-$ arising from the one-electron reduction of oxygen molecule, acts as an important protective factor in the body. For example, once the body is invaded by undesirable bacteria, virus, foreign matters or the like, phagocytes such as neutrophils, monocytes and macrophages are activated to exhibit dynamic functions such as migration and phagocytosis. Then, lysozomal enzyme and superoxide are resultingly yield and secreted to get involved directly or indirectly with the lysis and sterilization actions of the phagocytes, which allows the body to be protected from the invading foreign adversary.

Conversely, the excessive presence of the superoxide in the body causes various tissue disorders. The superoxide is generated in the body generally at the rate of 1% or less of oxygen absorbed into the body through respiration, and the generated superoxide is successively scavenged by the catalytic action of superoxide dismutase (SOD) contained in cells. However, if enzymatic actions are degraded as in an aged body, high concentration of the superoxide will be exhibited due to insufficient scavenging function. This leads to tissue disorders such as articular rheumatism or Behcet's Syndrome, or another symptoms arising from superoxide or lipoperoxide generated by the superoxide, such as myocardial infarction, cerebral apoplexy, cataract, blotches, freckles, wrinkles, diabetes, arterial sclerosis, stiff neck, or feeling of cold.

For example, some publications including Japan Patent No.2667959 propose a cosmetic containing superoxide dismutase. Unfortunately, any cosmetic containing the superoxide dismutase has not been commercially successful because such an enzyme is subjected to deactivation resulting from its instability to heat and is extremely expensive.

An approach for exploring a suitable material having the action of scavenging superoxide other than the superoxide dismutase is described in Japanese Patent Laid-Open Publication No. Sho 64-50877, in which baicalein contained in Scutellaria root is used. However, only a small amount of baicalein is contained in Scutellaria root. Thus, even if a sufficient amount of baicalein is successively extracted, an overdear product will be provided.

SUMMARY OF THE INVENTION

In view of the aforementioned problems, it is therefore an object of the present invention to provide a cosmetic comprising a superoxide scavenger including a desirable material which is different from any conventional unstable superoxide dismutase and is available at a low cost.

In order to achieve the above object, according to a first aspect of the present invention, there is provided a cosmetic comprising a superoxide scavenger including a composition extracted from a specific liquid prepared by: boiling a grain with a liquid to obtain a grain liquor; cooling the obtained grain liquor; adding a yeast into the cooled grain liquor; leaving the grain liquor with the yeast while supplying oxygen thereto; and sterilizing the resulting liquid by heating to obtain the specific liquid. Preferably, a bean is used as the grain.

According to a second aspect of the present invention, there is provided a cosmetic including a specific liquid prepared by: boiling a grain with a liquid to obtain a grain liquor; cooling the obtained grain liquor; adding a yeast into the cooled grain liquor; leaving the grain liquor with the yeast while supplying oxygen thereto; and sterilizing the resulting liquid by heating to obtain the specific liquid. In this case, it is also preferable that a bean is used as the grain.

In the first and second aspects of the present invention, the cosmetic may be either one of a facial cleaner, a skin lotion and a gel cosmetic.

The superoxide scavenger used in the cosmetic of the present invention can be stably remained even under a temperature of 80° C. or more. Further, using grains as a main ingredient allows the superoxide scavenger to be provided at a lower cost than that of any other conventional superoxide scavengers.

Other features and advantages of the present invention will be apparent from the following description.

DESCRIPTION OF THE PREFERRED EMBODIMENTS

A cosmetic of the present invention comprises a superoxide scavenger including a composition extracted from a specific liquid prepared by: boiling a grain with a liquid to obtain a grain liquor; cooling the obtained grain liquor; adding a yeast into the cooled grain liquor; leaving the grain liquor with the yeast while supplying oxygen thereto; and sterilizing the resulting liquid by heating to obtain the specific liquid.

It is believed that the superoxide scavenger used in the cosmetic of the present invention scavenges superoxide based on the reaction of $2O_2^- + 2H^+ \rightarrow H_2O_2 + O_2$. However, it has not been elucidated that what kind of plant extract in the ingredient could scavenge superoxide.

In manufacturing the superoxide scavenger used in the cosmetic of the present invention, a suitable grain may include bean, rice, wheat, corn, barnyardgrass, millet or the like. Preferably, a suitable bean includes soy bean, butter bean, red bean, peanut, fava bean, pea, horsebean, cowpea or the like. In order to obtain the grain liquor, 1 to 20 parts of water by weight is first added to 1 part of at least one selected grain. Then, the grain with water is boiled for 30 minutes or more, preferably for 30 minutes to 5 hours. The resulting liquid or hot grain liquor is naturally cooled or self-cooled and then the cooled liquid is filtered to obtain a desired initial grain liquor.

A suitable amount of yeast is added to the initial grain liquor, and the grain liquor with the yeast is left for about 1 to 6 months while supplying oxygen thereto. Preferably, suitable yeast includes any yeast belonging to Saccharomyes, such as beer yeast, wine yeast, sake yeast, or baker's yeast.

In a preferred embodiment, about 10 ml of the initial grain liquor may be first poured into a test tube at room temperature. Then, the yeast may be added into this liquor, and the liquor with the yeast may be left for 1 to 10 days to obtain a first intermediate liquid. Then, 100 ml of the initial grain liquor may be poured into a flask, and the first intermediate liquid may be added into this liquor. The liquor with the first intermediate liquid may be left for 1 to 10 days to obtain a second intermediate liquid. Then, 100 liters of the initial grain liquor may be poured into a tank, and the second intermediate liquid may be added into this liquor, followed by leaving the liquor with the second intermediate liquid for about 1 to 6 months to obtain a stock solution of superoxide scavenger.

The resulting stock solution of superoxide scavenger is sterilized by heating at about 70 to 130° C. for about 2 seconds to 60 minutes. While this sterilized stock solution of superoxide scavenger can be used as a superoxide scavenger as-is, it may be concentrated and further dried under a reduced pressure to use as a dried extract, if necessary.

In the cosmetic of the present invention, the stock solution of superoxide scavenger is preferably used as a substitute for a part or all of water to be contained in various cosmetics. Thus, a required content of the stock solution of superoxide scavenger will be varied depending on the type of cosmetics. For example, when the cosmetic is used in the form of a skin lotion, the stock solution of superoxide scavenger may be contained at about 0.001 to 50.0% by weight, particularly at about 0.01 to 30.0% by weight.

EXAMPLE

In manufacturing the cosmetic of the present invention, a superoxide scavenger was first produced by the following process. For producing the superoxide scavenger, soybean was selected from beans as the grain. First, 600 g of soybeans were immersed in 300 liters of water, and the soybeans with water were left for 10 hours. Then, 100 liters of water was further added to the soybeans with water, and the beans with the increased water were boiled in a pan for 5 hours. Then, the boiled beans and water were naturally cooled or self-cooled. Then, the soybeans were removed to obtain an initial liquor of about 200 liters.

10 ml of the initial liquor was poured in to a test tube, and a suitable amount of sake yeast was added into the liquor. Then, the liquor with the sake yeast was left at room temperature (The following process was also carried out at room temperature. An average room temperature in one month and 4 days required for the completion of the stock solution of superoxide scavenger was 26° C.) for 2 days to obtain a first intermediate liquid. In the course of this operation, the liquor with the sake yeast was agitated at intervals to supply oxygen thereto.

Then, 100 ml of the initial liquor was poured into a flask, and the first intermediate liquid was added into this liquor. The liquor with the first intermediate liquid was left at room temperature for 2 days to obtain a second intermediate liquid. In the course of this operation, the liquor with the first intermediate liquid was also agitated at intervals to provide oxygen thereto. Then, the obtained second intermediate liquid was poured into the remaining initial liquor, and this liquor with the second intermediate liquid was left for 1 months. In the course of this operation, the liquor with the second intermediate liquid was also agitated at intervals to provide oxygen thereto.

According to the food heat-sterilization process defined by the Public Health Department Regulations, the obtained liquid was sterilized by heating at 85° C. for 30 minutes to obtain a stock solution of superoxide scavenger of the present invention. Using the obtained the stock solution of superoxide scavenger, a superoxide scavenging activity was determined as described below.

1. Measuring Method

Superoxide (activated oxygen) was generated by the hypoxanthine-xanthine oxidase system, and each sample to be measured was added into the obtained superoxide. Then, the superoxide scavenging activity (SOSA) for each sample was determined from the signal strength of ESR (electron spin resonance) spectrum obtained by using the spin-trap process. DETAPAC (di-ethylen triamine penta acetic acid) was added to eliminate metallic impurities.

2. Measuring Equipment and Measuring Condition

Using the ESR JES-REIX made by JEOL Ltd., the measurement was carried out under the following condition.

Observation magnetic field: 355.4$\pm$ 5 mT

Microwave output: 8 mV

Magnetic field modulation amplitude: 0.079 mT

Sweep time: 2 min

Microwave frequency: 100 kHz

The stock solution of superoxide according to the invention had a SOSA value of 20.1 unit/ml. Up to now, various comparative measurement values of the superoxide scavenging activity have been obtained, such as 0.2 unit/ml for tap water, 3.8 unit/ml for (pH 8.0) ionized alkaline water, 5.7 unit/ml for (pH 9.0) ionized alkaline water, and 3.6 unit/ml for magnetic water. Since the reproducibility of the measurements is $\pm$ 0.5 unit/ml, it was verified that in the comparison of liquid to liquid, the stock solution of superoxide scavenger of the present invention had a higher superoxide scavenging activity than that of others. While the superoxide dismutase (Cu—Zu type SOD) made by Wako Pure Chemical Industries, Ltd. has a superoxide scavenging activity value of 3000 to 4000 unit/mg, it is not practicable to compare each superoxide scavenging activities of a solid superoxide scavenger, such as the above superoxide dismutase, and a liquid superoxide scavenger, such as the superoxide scavenger of the present invention, at this time.

In terms of the superoxide scavenging activities of the stock solution of superoxide scavenger described above, it can be expected that the cosmetic containing the stock solution of superoxide scavenger may exhibit skin conditioning and whitening effects including effects of eliminating blotches, freckles and wrinkles caused by superoxide. Specific examples will be described as follows.

Example 1

Face Cleaner

2% by weight of the stock solution of superoxide quencher obtained by the above process, NMF (natural moisturizing factor) composition, collagen, amino acid, seaweed extract, royal jelly extract, glycyrrhiza composition, natural vitamin E, rose fruit extract, sophorae radix (sophora flavescens) extract, mulberry bark extract, peony extract, cat's ear extract, bio anti-age (aloe extract, chlorella extract, puerariae radix extract), saxifrage extract, extract of peony root bark, hop extract, rosemary extract, pine tree extract, lemon extract, field horsetail extract, burdock extract, salvia extract, watercress extract, ivy extract, soapwort extract, orange oil, flavo-steron, labiate extra, olive oil.

Example 2

Skin Lotion

2% by weight of the stock solution of superoxide quencher obtained by the above process, bifidobacteria extract, NMF (natural moisturizing factor) composition, amino acids, collagen, hyaluronic acid, elastin, silk protein, royal jelly extract, rehmanniae radix extract, ginseng extract, hoelen extract, rose fruit extract, mulberry bark extract, peony extract, Japanese angelica extract, bio anti-age (aloe extract, chlorella extract, puerariae radix extract), fennel extract, watercress extract, horse chestnut extract, burdock extract, soapwort extract, sage extract, ivy extract, lemon extract, flavo-steron, saxifrage extract, cat's ear extract, seaweed extract, hop extract, rosemary extract, pine tree extract, field horsetail extract, vitamin B derivatives, vitamin BI, fruit acid, orange oil.

Example 3

Gel Cosmetic

2% by weight of the stock solution of superoxide quencher obtained by the above process, bifidobacteria extract, NMF (natural moisturizing factor) composition, collagen, amino acids, glycyrrhiza composition, phospholipide, vitamin B derivatives, vitamin $B_6$, natural vitamin E, allantoin, bio anti-age (aloe extract, chlorella extract, puerariae radix extract), jojoba oil, squalen, seaweed extract, cat's ear extract, rose fruit extract, mulberry bark extract, peony extract, Japanese angelica extract, rehmanniae radix extract, ginseng extract, hoelen extract, field horsetail extract, hops extract, pine tree extract, rosemary extract, lemon extract, royal jelly extract, flavo-steron, saxifrage extract, moutan bark extract, labiate extract, paprika extract, fruit acid.

The invention has now been explained with reference to specific embodiments. Other embodiments will be apparent to those of ordinary skill in the art. Therefore, it is not intended that the invention be limited, except as indicated by the appended claims, which form a part of this invention description.

What is claimed is:

1. A composition comprising a cosmetic and a superoxide scavenger concentrate which is obtained by concentrating said superoxide scavenger from a specific liquid, wherein said specific liquid is prepared by:
   (1) boiling a grain with water to obtain a grain liquor;
   (2) cooling said obtained grain liquor;
   (3) adding a yeast belonging to Saccharomyes into said cooled grain liquor;
   (4) leaving said grain liquor with said yeast while supplying oxygen thereto for about 1 to 6 months, or leaving a small amount of said grain liquor with said yeast while supplying oxygen thereto for about 1 to 6 days to obtain an intermediate liquid, and then leaving said grain liquor with said intermediate liquid while supplying oxygen thereto for about 1 to 6 months; and
   (5) sterilizing the resulting liquid by heating to obtain said specific liquid; wherein the grain is a bean; and said cosmetic comprises one or more ingredients selected from the group consisting of collagen, amino acids, seaweed extract, royal jelly extract, glycyrrhiza composition, natural vitamin E, Rose fruit extract, sophorae radix extract, mulberry bark extract, peony extract, cat's ear extract, aloe extract, chlorella extract, puerariae radix extract, saxifrage extract, extract of peony root bark, hop extract, rosemary extract, pine tree extract, lemon extract, field horsetail extract, burdock extract, salvia extract, watercress extract, ivy extract, soapwort extract, orange oil, labiate extract, and olive oil.

2. A composition as defined in claim 1, wherein said bean is a soybean.

3. A composition as defined in claim 1, wherein said cosmetic is a facial cleaner.

4. A composition as defined in claim 1, wherein said cosmetic is a skin lotion.

5. A composition as defined in claim 1, wherein said cosmetic is a gel cosmetic.

6. A composition comprising a cosmetic and a specific liquid prepared by:
   (1) boiling a grain with water to obtain a grain liquor;
   (2) cooling said obtained grain liquor;
   (3) adding a yeast belonging to Saccharomyes into said cooled grain liquor;
   (4) leaving said grain liquor with said yeast while supplying oxygen theretofor about 1 to 6 months, or;
   leaving a small amount of said grain liquor with said yeast while supplying oxygen thereto for about 1 to 6 days to obtain an intermediate liquid, and then leaving said grain liquor with said intermediate liquid while supplying oxygen thereto for about 1 to 6 months; and
   (5) the resulting liquid by heating to obtain said specific liquid,
   wherein said grain is a bean; and
   said cosmetic comprises one or more ingredients selected from the group consisting of collagen, amino acids, seaweed extract, royal jelly extract, glycyrrhiza composition, natural vitamin E. rose fruit extract, sophorae radix extract, mulberry bark extract, peony extract, cat's car extract, aloe extract, chlorella extract, puerariae radix extract, extract of peony root bark, hop xtract, salvia extract, watercress extract, ivy extract, soapwort extract, orange oil, labiate extract, and olive oil.

7. A composition as defined in claim 6, wherein said bean is a soybean.

8. A composition as defined in claim 6, wherein said cosmetic is a facial cleaner.

9. A composition as defined in claim 6, wherein said Cosmetic is a skin lotion.

10. A composition as defined in claim 6, wherein said cosmetic is a gel cosmetic:.

* * * * *